US 6,740,882 B2

(12) United States Patent
Weinberg

(10) Patent No.: US 6,740,882 B2
(45) Date of Patent: May 25, 2004

(54) DEDICATED APPARATUS AND METHOD FOR EMISSION MAMMOGRAPHY

(75) Inventor: Irving Weinberg, Bethesda, MD (US)

(73) Assignee: Naviscan PET Systems, Inc., Rockville, MD (US)

( * ) Notice: Subject to any disclaimer, the term of this patent is extended or adjusted under 35 U.S.C. 154(b) by 0 days.

(21) Appl. No.: 10/278,096

(22) Filed: Oct. 23, 2002

(65) Prior Publication Data

US 2003/0038240 A1 Feb. 27, 2003

Related U.S. Application Data

(60) Division of application No. 09/733,680, filed on Dec. 8, 2000, now Pat. No. 6,545,280, which is a continuation of application No. 09/415,979, filed on Oct. 12, 1999, now Pat. No. 6,229,145, which is a continuation of application No. 08/811,915, filed on Mar. 5, 1997, now Pat. No. 5,965,891, which is a continuation of application No. 08/647,555, filed on May 14, 1996, now abandoned, which is a continuation of application No. 08/262,737, filed on Jun. 20, 1994, now Pat. No. 5,519,221, which is a continuation-in-part of application No. 08/063,450, filed on May 18, 1993, now Pat. No. 5,323,006, which is a continuation-in-part of application No. 07/824,804, filed on Jan. 22, 1992, now Pat. No. 5,252,830.

(51) Int. Cl.$^7$ ................................................ G01T 1/161
(52) U.S. Cl. .............................. 250/363.02; 250/363.03
(58) Field of Search ...................... 250/363.02, 363.03, 250/363.04; 378/37, 25, 26; 600/310, 407, 411

(56) References Cited

U.S. PATENT DOCUMENTS

| | | | |
|---|---|---|---|
| 4,135,089 A | 1/1979 | McIntyre | |
| 4,981,142 A | 1/1991 | Dachman | |
| 5,046,498 A | 9/1991 | Fishman | |
| 5,051,257 A | 9/1991 | Pietronigro | |
| 5,077,034 A | 12/1991 | Kassis et al. | |

(List continued on next page.)

FOREIGN PATENT DOCUMENTS

| | | |
|---|---|---|
| EP | 093017620 | 9/1983 |
| JP | 5510589 | 8/1981 |
| JP | 59-180477 | 10/1984 |
| WO | WO-93/17620 A1 | 9/1993 |

Primary Examiner—Scott J. Sugarman
Assistant Examiner—Richard Hanig
(74) Attorney, Agent, or Firm—Katten Muchin Zavis Rosenman

(57) ABSTRACT

The present invention is an apparatus for examining a body part. The apparatus comprises a mechanism for immobilizing and compressing the body part. The apparatus also comprises a mechanism for providing an internal anatomical image of the body part and a mechanism for detecting single gamma-rays emitted by a radiotracer infiltrated into the body part. The detecting mechanism is disposed in an adjacent relationship with the mechanism for providing an internal anatomic image so that the body part remains in the same position during and between anatomic and radiotracer imaging. In one embodiment, the detecting mechanism includes a detector module disposed on one side of the immobilizing mechanism. The detector module preferably has at least one array of gamma ray sensitive material in communication with a position detector. In another embodiment, the detecting mechanism includes a pair of detector modules disposed one on each side of the immobilizing mechanism. The present invention is also an apparatus for examining a body part which comprises a mechanism for immobilizing and compressing the body part and a mechanism for providing a stereotactic internal anatomical image of the body part. The apparatus also comprises a mechanism for providing a stereotactic physiological image of the body part in an adjacent relationship with the mechanism for providing an internal anatomic image such that the body part remains in the same position during and between stereotactic anatomic and radiotracer imaging.

13 Claims, 8 Drawing Sheets

U.S. PATENT DOCUMENTS

| | | |
|---|---|---|
| 5,219,351 A | 6/1993 | Trubner et al. |
| 5,252,830 A | 10/1993 | Weinberg |
| 5,308,352 A | 5/1994 | Koutrouvelis |
| 5,323,006 A | 6/1994 | Thompson et al. |
| 5,519,221 A * | 5/1996 | Weinberg .............. 250/363.02 |
| 5,931,774 A * | 8/1999 | Williams et al. ................ 600/2 |
| 6,229,145 B1 | 5/2001 | Weinberg |

* cited by examiner

DEDICATED APPARATUS AND METHOD FOR EMISSION MAMMOGRAPHY

CROSS REFERENCE

This is a divisional application of U.S. Ser. No. 09/733,680, filed Dec. 8, 2000 Now U.S. Pat. No. 6,545,280, which is a continuation of U.S. Ser. No. 09/415,979, filed Oct. 12, 1999, now U.S. Pat. No. 6,229,145, issued May 8, 2001, which is a continuation of U.S. Ser. No. 08/811,915, filed Mar. 5, 1997, now U.S. Pat. No. 5,965,891, issued Oct. 12, 1999, which is a continuation of U.S. Ser. No. 08/647,555, filed May 14, 1996, now abandoned, which is a continuation of U.S. Ser. No. 08/262,737, filed Jun. 20, 1994, now U.S. Pat. No. 5,519,221, issued Jun. 21, 1996, which is a continuation-in-part application of U.S. Ser. No. 08/063,450, filed May 18, 1993, now U.S. Pat. No. 5,323,006, issued Jun. 21, 1994, which is a continuation-in-part of U.S. Ser. No. 07/824,804, filed Jan. 22, 1992, now U.S. Pat. No. 5,252,830, issued Oct. 12, 1993.

FIELD OF THE INVENTION

The present invention is related to an apparatus for medical examination. More specifically, the present invention is related to an apparatus and method for imaging the radiotracer concentration in a female breast or other organ.

BACKGROUND OF THE INVENTION

Mammography is currently the most effective method of screening for breast cancer. The goal of breast cancer screening is the detection of early non-palpable tumors. Although mammography is very sensitive in the detection of cancer, it is not very specific in determining whether mammographic abnormalities are due to benign or malignant disease (Limitations of Mammography in the Identification of Noninfiltrating Carcinoma of the Breast, S. F. Sener, F. C. Candela, M. L. Paige, J. R. Bernstein, D. P. Winchester, *Surgery, Gynecology, and Obstetrics*, August 1988, 167:135–140). Therefore, a noninvasive method of confirming the malignancy of suspicious mammographic abnormalities would be a major benefit in patient care. In this way, the number of benign excisional biopsies (approximately 75% of all excisional biopsies) can be reduced.

When abnormal mammograms are encountered, the physician's options are limited. For minimally suspicious lesions, short-term repeat examination (four to six month follow-up) is often recommended. This may result in psychological stress for the patient and introduces the possibility of loss in patient follow-up due to scheduling or communication errors. The unlikely possibility of interim tumor growth cannot be definitely ruled out (Breast Cancer: Age-Specific Growth Rates and Screening Strategies, M. Moskowitz, *Radiology*, October 1986, 161:37–41), especially in patients under fifty.

The role of ultrasound in clarifying the status of a mammographic abnormality is limited to the differentiation of solid masses from benign cysts. If the strict criteria for the ultrasonic appearance of a simple cyst are satisfied, the referring physician may be reassured that the lesion is benign. Unfortunately, the current spatial resolution of ultrasound makes the technique of limited value for lesions significantly smaller than five millimeters.

Doppler ultrasound has been advocated as a means for differentiating benign from malignant masses, but results of clinical trials have been contradictory, and the doppler method has no current clinical role in breast imaging (The Role of US in Breast Imaging, V. P. Jackson, *Radiology*, November 1990, 177:305–311).

Fine-Needle Aspiration (FNA) of breast masses is a technique whose sensitivity and specificity is operator dependent (Fine-Needle Aspiration Biopsies of Breast Masses, L. Palombini et al., *Cancer*, Jun. 1, 1988, 61:2273–2277), and has been considered experimental (Discriminating Analysis Uncovers Breast Lesions, D. B. Kopans, *Diagnostic Imaging*, September 1991, pp. 94–101). Because of its relatively low cost and reduced morbidity associated with surgery and anesthesia, FNA has been suggested as a possible replacement for excisional biopsy. Unfortunately, there is a high (13–50%) rate of insufficient samples when FNA is performed on non-palpable mammographically detected lesions. All of these cases of negative FNAs require excisional biopsy (Fine-Needle Aspiration Cytology in Lieu of Open Biopsy in Management of Primary Breast Cancer, H. J. Wanebo et al., *Annals of Surgery*, May 1984, 199 (5) pp. 569–579). Further, FNA as a non-imaging diagnostic modality, has the disadvantage that no information is obtained about the physical distribution of the detected tumor. As a cytopathological technique, FNA cannot easily differentiate between cases of marked dysplasia, carcinoma-in-situ, or invasive cancer. Fine-Needle Aspiration is generally not performed for non-palpable breast lesions.

Another option for the referral of a patient with equivocal mammographic anomalies is excisional biopsy of the breast in the area corresponding to the region of mammographic abnormality. The probability of malignancy ranges from 2% for a circumscribed solid mass to almost 90% for a spiculated ill-defined mass (Discriminating Analysis Uncovers Breast Lesions, D. B. Kopans, *Diagnostic Imaging*, September 1991, pp. 94–101. The true-positive fraction for biopsies obtained as a result of a mammographic screening program is between twenty and thirty percent (Nonpalpable Breast Lesions: Accuracy of Prebiopsy Mammographic Diagnosis, G. Hermann, C. Janus, I. S. Schwartz, B. Krivisky, S. Bier, J. G. Rabinowitz, *Radiology*, November 1987 165:323–326; R. Brem, personal communication). Excisional biopsy has the additional disadvantage of introducing scarring, which may render interpretation of follow-up mammograms more difficult (Discriminating Analysis Uncovers Breast Lesions, D. B. Kopans, *Diagnostic Imaging*, September 1991, pp. 94–101). An additional disadvantage to excisional biopsies is that, as a non-imaging modality, the physical distribution of the tumor is poorly described.

It is also possible to use radionuclide imaging to detect cancers. 2-[F-18]-Fluoro-2-deoxy-D-glucose (FDG) is a radioactive analogue of glucose that is taken up preferentially by cancer cells (Primary and Metastatic Breast Carcinoma: Initial Clinical Evaluation with PET with the Radiolabeled Glucose Analogue 2-[F-18]-Fluoro-2-deoxy-D-glucose, R. L. Wahl, R. L. Cody, G. D. Hutchins, E. E. Mudgett, *Radiology* (1991) 179:765–770). A Fluorine-18 nucleus decays by emitting a positron which is annihilated within a millimeter by an electron. The result of this annihilation is the production of two 511 kev (thousand electron volts) gamma rays that are approximately 180 degrees apart in direction. After a patient has received an intravenous dose of FDG she may be examined with detectors that sense these gamma rays.

Previous detection methods have included imaging with a specially collimated planar gamma camera ([18-F] Fluorodeoxyglucose scintigraphy in diagnosis and follow up of treatment in advanced breast cancer, *European Journal of*

*Nuclear Medicine* (1989) 15:61–66) and with a whole-body Positron Emission Tomography (PET) scanner (Primary and Metastatic Breast Carcinoma: Initial Clinical Evaluation with PET with the Radiolabeled Glucose Analogue 2-[F-18]-Fluoro-2-deoxy-D-glucose, R. L. Wahl, R. L. Cody, G. D. Hutchins, E. E. Mudgett, *Radiology* (1991) 179:765–770). PET imaging of breast cancer patients given FDG has been shown to be useful in imaging tumors as small as 3.2 cm and in patients whose breasts are too dense to be imaged well mammographically (Primary and Metastatic Breast Carcinoma: Initial Clinical Evaluation with PET with the Radiolabeled Glucose Analogue 2-[F-18]-Fluoro-2-deoxy-D-glucose, R. L. Wahl, R. L. Cody, G. D. Hutchins, E. E. Mudgett, *Radiology* (1991) 179:765–770).

The use of a specially collimated planar gamma camera to image the breast with this high resolution is limited by technical factors. The energy of 511 KeV is too penetrating to be detected well by conventional gamma cameras, and the collimation required to correct for the high energy leads to loss of signal (counts/pixel) that is equivalent to resolution loss due to low photon flux.

Conventional PET imaging devices are designed to image cross sections of the entire body. Accordingly, there are several disadvantages to employing a whole body PET scanner in a primary role as a high resolution confirmatory modality for small suspicious breast lesions. The first disadvantage of using a whole body PET scanner for breast imaging is the limited resolution available. The net resolution of a whole-body PET system is a combination of individual factors and is limited to above 5 mm FWHM (E. Rota-Kops et al., Journal of Computer Assisted Tomography 1990, May–June 14 (3), pages 437–445; N. A. Mullani et al., Journal of Nuclear Medicine 1990, May 31 (5), pages 610–616 and pages 628–631; K. Wienhard et al., Journal of Computer Assisted Tomography 1992, September–October 16 (5) pages 804–813). The effect of this resolution limit is that radioactivity is underestimated (Positron Emission Tomography and Autoradiography, Edited by M. E. Phelps, J. C. Mazziotta, H. R. Schelbert, pp. 240–285, Raven Press, N.Y. 1986; Design of a Mosaic BGO Detector System for Positron CT, H. Uchida, T. Yamashita, M. Iida, S. Muramatsu, *IEEE Transactions on Nuclear Science* February 1986, NS-33 (1), pp. 464–467). This reduces the sensitivity of PET scanners in estimating the malignancy of mammographically detected lesions smaller than twice the resolution limit, and also precludes the use of the PET scanner in delineating tumor margins with high accuracy.

A second disadvantage of a conventional PET scanner for imaging of subtle lesions in the breast is the high cost of the examination. In order to accommodate the entire body, a conventional PET scanner must employ tens or hundreds of expensive detector arrays along with a gantry and associated electronics.

A third disadvantage of a PET scanner is that the PET image format would not be easily compared to conventional mammograms. This is due to the fact that the breast is an organ which can be compressed to an essentially two-dimensional object. The variability in internal architecture of the breast results in few landmarks for positioning, and the location of an anomaly on the mammographic image of the compressed breast does not always correspond to the same location in the non-compressed breast.

In order to achieve the highest spatial resolution available in a tomographic system, motion of the patient due to breathing must be limited. Immobilizing of the breast by compression is the most straightforward approach to solving this problem, but implementation within a PET scanner detector ring is difficult. Additionally, the use of PET scanner to image an essentially two-dimensional object such as a compressed breast is not economically rational.

High resolution (20 cm diameter bore) PET scanners, originally developed for animal studies, may soon be available commercially. For a system with smaller aperture (i.e. 20 cm bore for a dedicated head scanner) the resolution in the axial plane is 3.5 mm (Development of a High Resolution PET, T. Yamashita et al., *IEEE Transactions on Nuclear Science*, April 1990, Vol. 37 (2) pp. 594–599). Such a system would satisfy the goal of high resolution. A disadvantage would be the considerable cost of such relatively expensive scanners, with approximately fifteen detector arrays, as dedicated units for breast imaging. Further, the problems of immobilization of the breast and of comparison to standard mammography would still be unaddressed.

SUMMARY OF THE INVENTION

The present invention is an apparatus for examining a body part. The apparatus comprises means or a mechanism for immobilizing and compressing the body part. The apparatus also comprises means or a mechanism for providing an internal anatomical image of the body part and means or a mechanism for detecting single gamma-rays emitted by a radiotracer infiltrated into the body part. The detecting mechanism is disposed in an adjacent relationship with the means or mechanism for providing an internal anatomic image so that the body part remains in the same position during and between anatomic and radiotracer imaging.

In one embodiment, the detecting means or mechanism includes a detector module disposed on one side of the immobilizing means or mechanism. The detector module preferably has at least one array of gamma ray sensitive material in communication with a position detector. In another embodiment, the detecting means or mechanism includes a pair of detector modules disposed one on each side of the immobilizing means or mechanism. Preferably, the means or mechanism for providing an anatomical image includes an x-ray source and x-ray recording medium.

The present invention is also an apparatus for examining a body part which comprises means or a mechanism for immobilizing and compressing the body part and means or a mechanism for detecting single gamma-rays emitted by a radiotracer infiltrated into the body part.

The present invention is also an apparatus for examining a body part which comprises means or a mechanism for immobilizing and compressing the body part and means or a mechanism for providing a stereotactic internal anatomical image of the body part. The apparatus also comprises means or a mechanism for providing a stereotactic physiological image of the body part in an adjacent relationship with the means or mechanism for providing an internal anatomic image such that the body part remains in the same position during and between stereotactic anatomic and radiotracer imaging.

Preferably, the means or mechanism for obtaining a stereotactic physiological image includes a pair of detector modules disposed one on each side of the immobilizing means or mechanism. In one embodiment, the detector modules are constructed to travel angularly about the body part to provide projection images of the body part from at least two different viewing angles. In another embodiment, the detector modules are stationary with respect to the body part and obtain multiple projection views of the body part.

The present invention is also an apparatus for examining a body part which comprises means or a mechanism for immobilizing and compressing the body part and means or a mechanism for providing a stereotactic physiological image of the body part.

The present invention is also a method for examining a body part. The method comprises the steps of immobilizing the body part in a preferred position such that the body part is compressed. Then there is the step of obtaining at least one physiological image of the body part. Preferably, before the immobilizing step, there is the step of injecting the patient with a radiotracer which emits gamma rays and the step of obtaining at least one physiological image includes the step of detecting gamma-rays with at least one detector module disposed on at least one side of the body part. If desired, after the step of obtaining at least one physiological image, there can be the step of directing a biopsy needle or gun into the body part 12 using at least one physiological image for guidance and placement. After the step of obtaining the image or images, there can then be the step of operating on the patient using the image or images for guidance, localization, and preferably confirmation that the tumor has been removed completely. After the operating step, there can be the step of obtaining at least one image of surgical specimens to identify the presence of and the borders of tumors.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1:
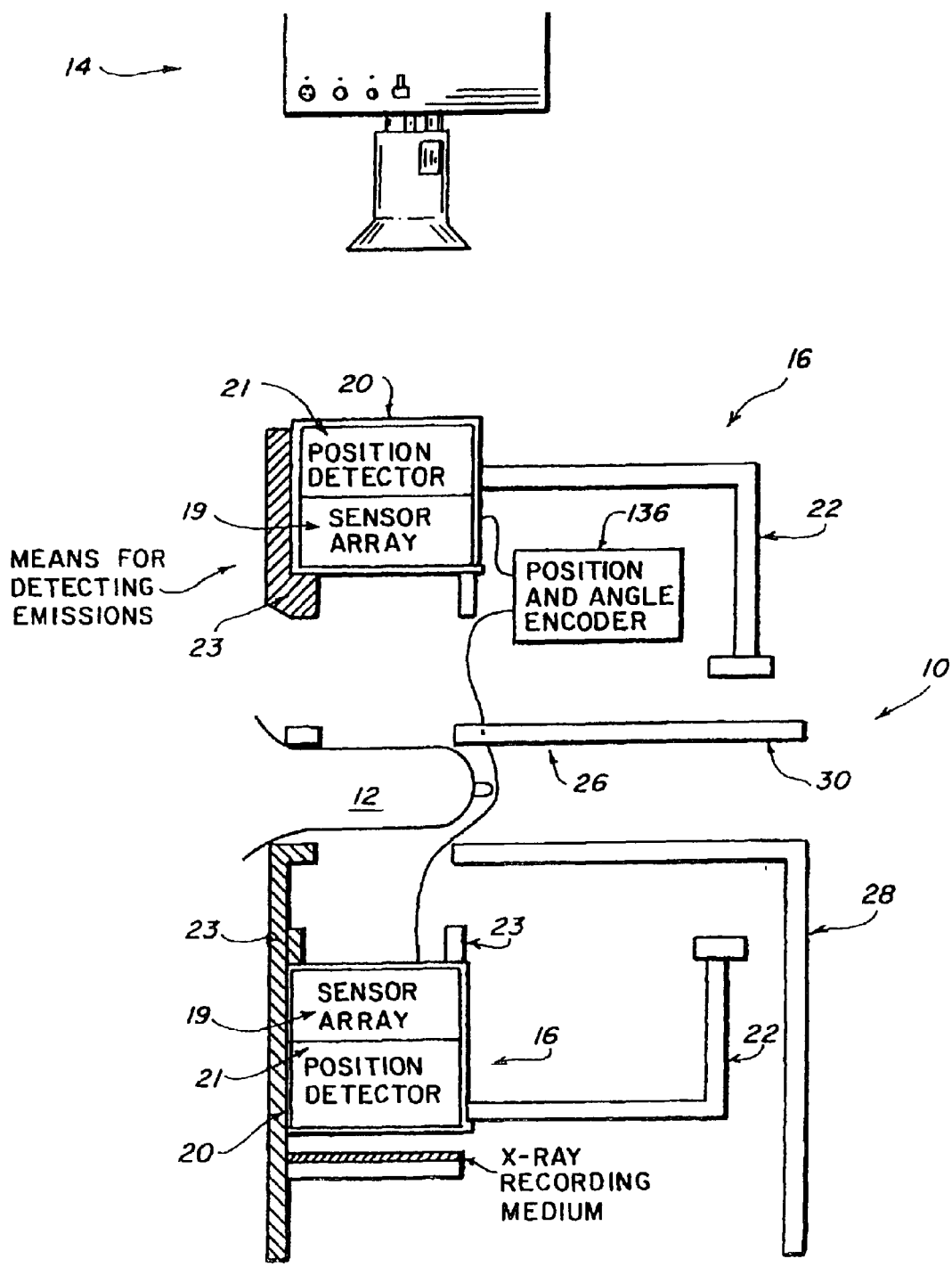
FIG. 1 is a schematic representation of an apparatus for examining a body part.

Referring now to the drawings wherein like reference numerals refer to similar or identical parts throughout the several views, and more specifically to FIG. 1 thereof, there is shown an apparatus 10 for examining a body part 12, such as a breast. The apparatus 10 includes means or a mechanism 14 for providing an anatomical image of the body part 12 and means or mechanism 16 for providing a physiological image of the body part 12. The means or mechanism 16 for providing a physiological image is disposed adjacent to the means or mechanism 14 for providing an anatomical image such that the body part 12 remains in the same position during and between anatomical and physiological imaging. Preferably, the body part 12 is infiltrated with a radiotracer and the means or mechanism 16 for providing a physiological image includes means or a mechanism for detecting emissions of the radiotracers from the body part 12. The radiotracers can be 2-[F-18]-fluoro-2-deoxy-D-glucose (FDG) or 16 alpha-[F-18]-fluoroestradiol-17 beta or other radiotracers. Preferably, the means or mechanism for providing an anatomical image includes an x-ray source and x-ray recording medium, such as x-ray film. Alternatively, a digital radiography device can be used. Alternatively, other methods of anatomic imaging such as magnetic resonance can be used. Alternatively, other methods of anatomic imaging such as ultrasound can be used.

In a preferred embodiment, the radiotracer produces gamma rays and the detecting means or mechanism includes two detector modules 20 each of which has at least one sensor array 19 of gamma ray sensitive material (scintillator), such as bismuth germanate (BGO) crystals, mounted upon a position detector 21 such as a photomultiplier array or position sensitive photomultiplier. Alternatively, individual light sensors, such as avalanche photodiodes can be mounted upon each gamma ray detector in the array 19. In an alternative embodiment, each detector module 20 has a continuous sheet of gamma ray detecting material which is mounted upon a position sensitive multiplier or photomultiplier array. The continuous sheet of gamma ray sensitive material can have slots with septa on its surface which would operate in a manner similar to the block detectors known in the art of PET scanners.

Preferably, each detector module 20 has dense shielding 23 for reducing undesirable emissions from other parts of the body. Preferably, each detector module 20 is attached to a swing arm 22 for allowing them to swing into and out of an operational portion. Preferably, the apparatus 10 includes means or a mechanism 26 for immobilizing the body part 12, such as with compression. The immobilizing means or mechanism 26 can include a table 28 and a compression arm 30 which compresses the body part 12 against the table 28.

In an alternative embodiment, the apparatus 10 is not limited to having means or a mechanism 14 for obtaining an anatomical image of the body part 12. The apparatus 10 includes means or mechanism 26 for immobilizing the body part 12 and means or mechanism 16 for providing a physiological image of the body part 12. The providing means or mechanism 16 is in an adjacent relationship to the immobilizing means or mechanism 26. Preferably, the immobilizing means or mechanism 26 compresses the body part 12 and can include a table 28 upon which the body part 12 rests and a compression arm 30 which compresses the body part against the table 28. Alternatively, the apparatus could include an immobilizing means or mechanism 26 consisting of a C-arm for intra-operative tumor localization.

The invention is also a method of examining a body part of a patient. The method includes the first step of immobilizing the body part in a preferred position. Then, there is the step of obtaining a physiological image of the body part. Preferably, before the immobilizing step, there is the step of injecting the patient with a radiotracer and the obtaining step includes the step of detecting emissions from the immobilized body part. The step of obtaining an anatomical image of the body part such as an x-ray can be performed before the immobilizing step. Preferably, before the immobilizing step, there is the step of performing a compression examination, such as a spot view compression examination.

The invention is also related to an alternative method of examining a body part of a patient. This method includes the first step of obtaining an anatomical image of the body part. Then, there is the step of obtaining a physiological image of the body part such that the body part remains in the same position during and between anatomical and physiological imaging. Preferably, before the obtaining step, there is the step of immobilizing the body part, such as with compression.

In the operation of the apparatus 10, a patient who is being examined for breast cancer would be injected with 2[F-18]-Fluoro-2-deoxy-D-glucose (FDG). FDG is a radiotracer which is a radioactive analogue of glucose that is taken up preferentially by breast cancer cells. A more detailed explanation of this process is given in Primary and Metastatic Breast Carcinoma: Initial Clinical Evaluation with PET with the Radiolabeled Glucose Analogue 2-[F-18]-Fluoro-2-deoxy-D-glucose, R. L. Wahl, R. L. Cody, G. D. Hutchins, E. E. Mudgett, *Radiology* (1991) 179:765–770, incorporated by reference. The isotope 18-F decays by emitting a positron which is annihilated within a few millimeters by an electron. The result of this annihilation is the production of two gamma rays that are approximately 180° apart in direction.

Approximately one hour after injection with FDG, the patient undergoes a spot view breast compression examination. The breast 12 would then be immobilized and a mammogram would be obtained for any areas suspicious for malignancy. If an abnormality is spotted on the mammographic film, high resolution detector modules 20 are swung in place above and below the compressed breast. Each detector module 20 consists of an array of bismuth germanate crystals which detect the gamma rays produced by the FDG. Each array is mounted upon a position sensitive photomultiplier. Electronic collimation using coincidence gating would yield high sensitivity to emitted radiation. The shielding reduces the number of undesirable emissions detected by the detector modules. Once the detector modules 20 are swung into place an image of the emissions is taken in areas of suspicion.

The rationale for the apparatus is the adaptation of the standard radiological mammographic geometry for the detection of gamma rays produced by positron-emitting and gamma-emitting radiotracers. The apparatus would incorporate (or be easily mounted upon) a conventional or x-ray mammography unit for straightforward comparison with conventional mammograms.

The increased sensitivity allowed by the mammographic geometry is expected to permit imaging of suspicious areas in the breast within a short period of time (10–15 minutes), allowing the patient to remain in breast compression for the duration of the scan. Use of the invention results in exact registration between the conventional mammogram and the image of radiotracer uptake. Advantages of the invention over existing technology include high resolution, low cost, reduced dose, and decreased morbidity.

The proximity of the detector modules to the breast in the proposed mammographic geometry will lead to resolution superior even to high resolution PET scanners. Since image reconstruction via filtered backprojection is not required in this geometry, no loss of resolution due to frequency filtering will be encountered.

The dose of radioactivity given to the patient will be similar to or less than the dose presently used for whole body PET imaging of FDG (approximately ten millicuries), which is within the acceptable radiation dose for diagnostic nuclear medicine techniques. The morbidity associated with this dose must be compared to the morbidity associated with unnecessary excisional biopsy. For treatment planning, the morbidity may be compared to that associated with unnecessary mastectomy. For delineation of tumor margin, the morbidity should be compared to the local recurrence of tumor in an under-resected breast.

Positron emitters such as Fluorine-18 (half-life 110 minutes) can be purchased by breast imaging centers from cyclotrons in most major U.S. cities. Note that the use of the proposed dedicated breast imaging device does not preclude the possibility of following the examination with a whole body PET scanner (if available) when clinically indicated, i.e., to search for metastases in a patient with proven cancer. Additionally, by placing a collimator upon one or both of the detector modules, and operating the apparatus in a non-coincident mode, the apparatus could be used in conjunction with more generally available radioisotopes that emit single photons. Additionally, the apparatus could be taken to the operating room for intra-operative tumor localization.

Figure 2:
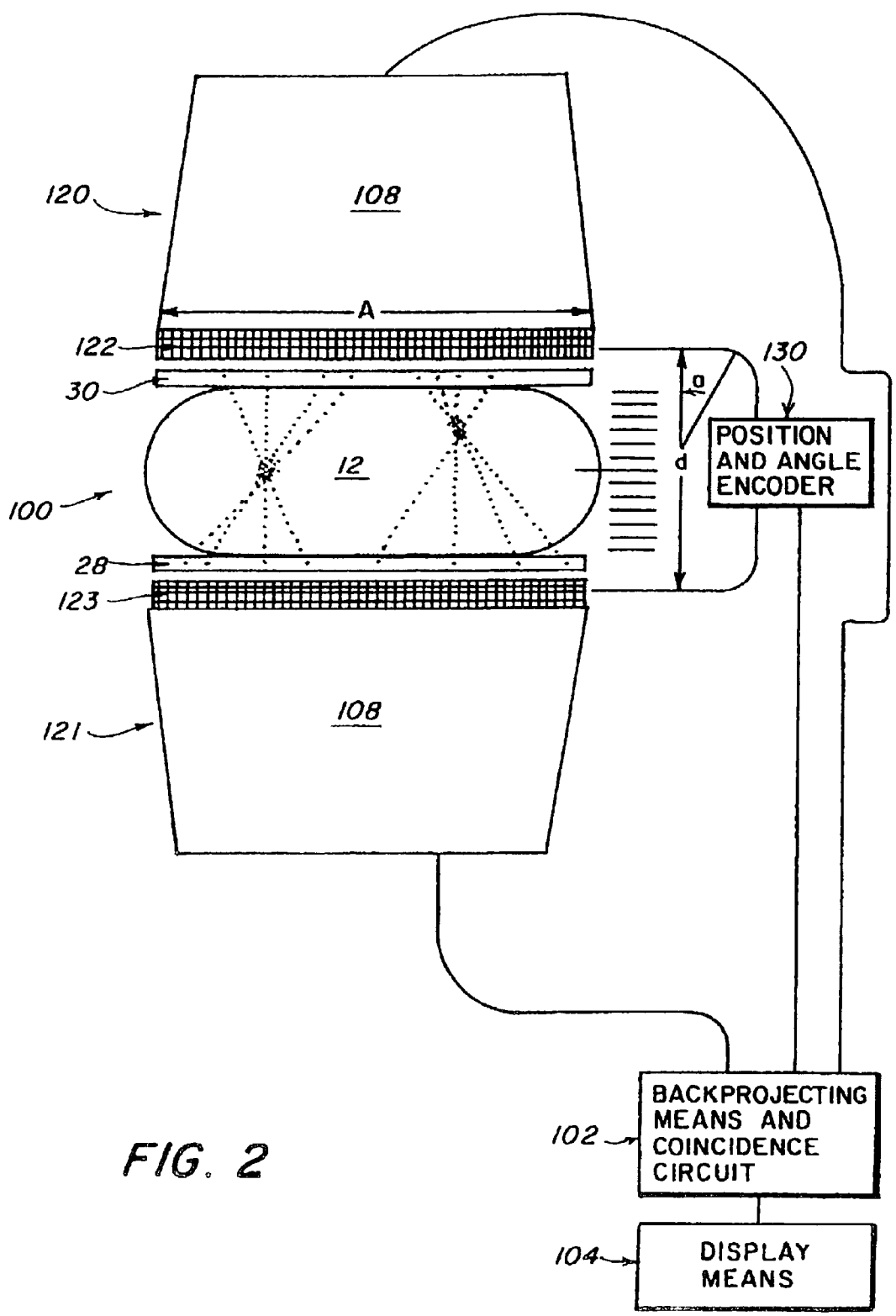
FIG. 2 is a schematic representation showing a close-up view of the detector modules of the apparatus for examining a body part.

If a radiotracer is used whose decay results in the production of opposing gamma rays, such as 2-[F-18]-Fluoro-2-deoxy-D-glucose, the present invention envisions an apparatus 100 which is capable of 3-dimensional imaging and offers optimal spatial resolution and sensitivity. As shown in FIG. 2, the apparatus 100 is comprised of a first detector module 120 for detecting radiotracer emissions from the body part 12 and a second detector module 121 for detecting radiotracer emissions from the body part 12. The first and second detector modules 120, 121 are disposed adjacent to each other with the body part 12 disposed therebetween. The apparatus 100 also comprises means or a mechanism 102 for backprojecting detected coincident events with respect to the first and second detector modules 120, 121 onto a plurality of imaging planes 132 between the first and second detecting modules 120, 121. The imaging planes 132 are shown in FIG. 4.

Preferably, the first detector module 120 is comprised of a first sensor array 122 of material sensitive to emissions from the radiotracer and the second detector module 121 is comprised of a second sensor array 123 of material sensitive to emissions from the radiotracer.

Figure 4:
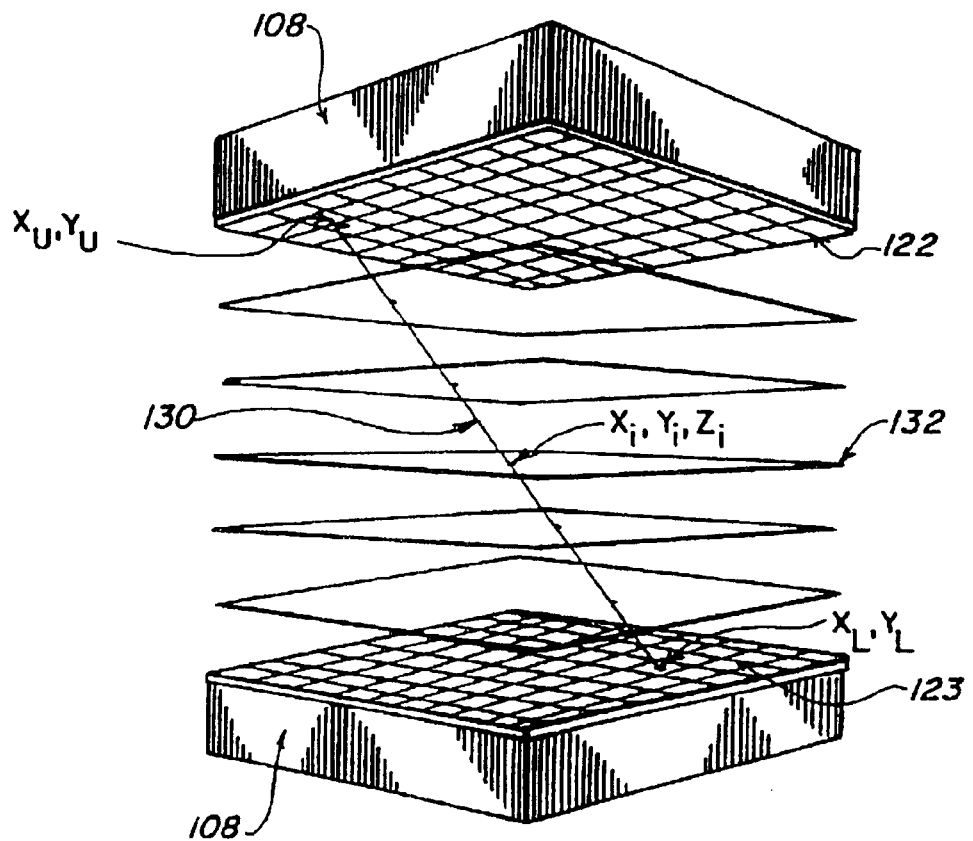
FIG. 4 is a schematic representation showing a plurality of imaging planes between the detector modules.

Preferably, as illustrated in FIG. 4, the backprojecting means or mechanism 102 comprises means or a mechanism for defining a line 130 between a point on the first sensor array 122 and a point on the second sensor array 123 associated with a coincident event and means or a mechanism for determining the intersection of the line 130 with each imaging plane 132. Preferably, the apparatus 100 also comprises means or a mechanism for determining the distance, d, and angle, a, between the first detector module 120 and the second detector module 121, such as a position and angle encoder 136. Preferably, each of the first and second detector modules 120, 121 comprises a position detector, such as imaging PMT (photo multiplier) 108. Preferably, the apparatus 100 also comprises means or a mechanism 104 for displaying the imaging planes such as a digital gamma camera display and acquisition system. Preferably, each of the sensor arrays 122, 123 are comprised of a large array of BGO crystals (20×20 to 40×40).

The present invention is also a method of examining a body part 12. The method comprises the step of detecting a plurality of coincident events associated with the interaction of radiotracer emissions from the body part 12 with a first and second sensor array 122 and 123. Then, there is the step of backprojecting the detected coincident events onto a plurality of imaging planes 132 between the first and second sensor arrays 122 and 123.

Preferably, the backprojecting step includes the step of defining a line 130 between a point of the first sensor array 122 and a second point of the second sensor array 123 associated with the coincident event and determining the intersection of the line 130 with each imaging plane 132. Preferably, after the backprojecting step, there is the step of displaying the plurality of imaging planes.

Figure 3A:
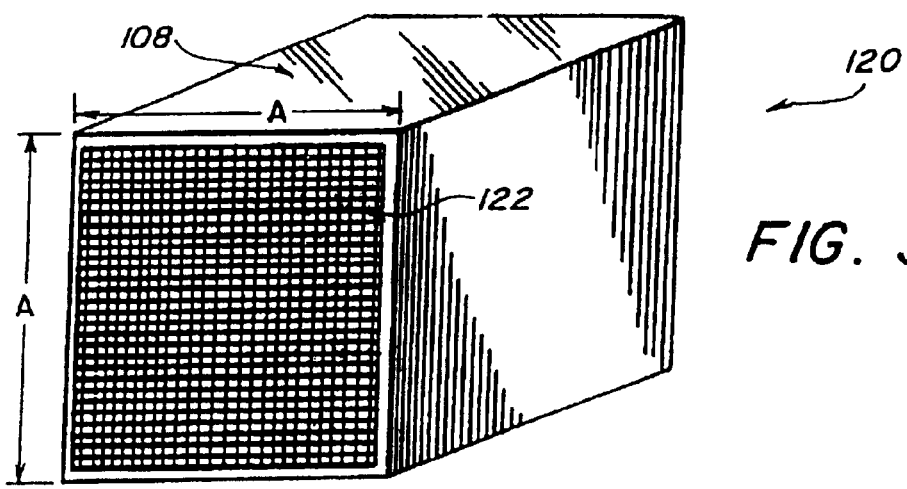
FIGS. 3a and 3b are schematic representations showing the arrangement of the sensor array on the Photomultiplier (PMT).
Figure 3B:
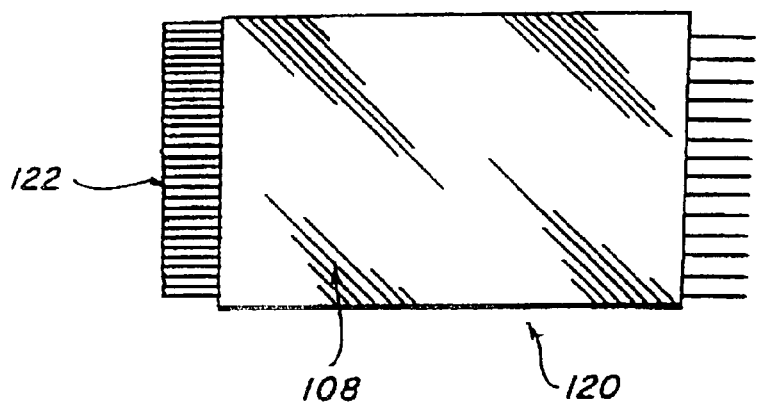

In the operation of the apparatus 100, the patient is injected with 2-[F-18]-flouro-2-deoxy-D-glucose (FDG). As shown in FIGS. 3a and 3b, each of the detector modules 120, 121 comprises a Hamamatsu R394I-02 Imaging PMT 108 with an array 122, 123 of 37×37 BGO crystals above and below a breast 12. The width of each array 122, 123 is 75 mm, as represented by reference character A. Each crystal is 2×2×7 mm. The top of each crystal is cut at the optimal angle 25° to break the symmetry to maximize the light collected by the PMT 108. The exact length (7 mm above) is a compromise between efficiency and resolution. One wishes to maximize the efficiency (make the crystals longer) while minimizing the multiple interactions which will blur the image (make the crystals shorter) ("Single Interaction PET Detectors" C. A. Burnham, J. T. Elliot, D. E. Kaufman, D. A. Chesler, J. A. Correia, and G. L. Brownell. Conference Record of the 1990 IEEE Nuclear Science Symposium PP: 1332–1336 1990, incorporated by reference.

This sensor array design is based on the belief that techniques which would measure the number of interactions are too complicated to be practical ("Resolution and Sensitivity Improvement in Positron Emission Tomography by the First Interaction Determination" Z. H. Cho and S. C. Juh. IEEE 1991 Medical Imaging Conference (Santa Fe) Record pp. 1623–1627). The effect of multiple interactions is reduced, by reducing the probability of their occurrence. This thin sensor array design will have reduced efficiency, but the other detection possibilities gained by allowing all crystals to be in coincidence will more than make up for this. Oblique rays would normally require the measurement of the depth of interaction in each crystal to maintain good spatial resolution ("A PET Detector with Depth-of-Interaction Determination" P. Bartzakos and C. J. Thompson. Phys. Med. Biol. V 36, pp. 735–748 (1991), but these crystals will be short enough to make this measurement unnecessary. Alternatively, a crystal block cut from the top and bottom with the bottom cuts offset from the top cuts by half the cut separation could be used to reduce the parallax error caused by oblique incidence on a deep detector.

The first and second detectors modules 120, 121 are separable by raising the upper one. The distance, d, between them would be variable in order to accommodate anatomical variations. The angle, a, between them would be variable to accommodate imaging of organs such as the prostate, that might require non-parallel arrangement of the detector modules.

Each imaging PMT 108 would be connected to three analog-to-digital converters (ADCs) to measure the X and Y coordinates and the observed energy of the gamma ray produced by the FDG radiotracer. The PMTs 108 would be connected to a coincidence circuit and the backprojecting means or mechanism 102 in order to detect the gamma rays produced by positron annihilations in the region between them. In principle coincidences between any crystal in the first and second sensor arrays 122, 123 will be permitted. It is from the diagonal coincidences, and the current detector module separation, d, and angle, a, that the depth of the event can be determined.

When an annihilation occurs between the first and second sensor arrays 122, 123 the 511 keV gamma pair may travel in such directions that they will interact with the first and second arrays 122, 123. As one ray enters a crystal it has a 20 to 30% chance of interacting with it, depending on the crystal depth and the photon direction. Of these events, 45% are photo-electric, depositing 511 kev in one crystal only. The shape of the crystals is such that most of the light photons created in such events are detected by the PMT 108, making good energy identification possible (Probably better than 10% full-width at half-maximum [FWHM] energy resolution). The Compton scattered rays from the other 55% of the interactions will be scattered onto a cone whose most probable apex angle is 45° and will deposit 50 keV in the crystal at a depth of 3 mm. The 461 keV ray will then escape and interact beyond the crystal. For this reason the electronics for event detection should be sensitive to the 511 kev photons from photo-electric events and 25–150 keV photons corresponding to single Compton interactions of 511 kev photons, and should be able to discriminate against the single Compton interactions on the basis of their lower energy.

If two such photons (one in each detector module) are detected within the resolving time, a coincidence has occurred, and a line corresponding to the most probable depth of interaction in the two crystals is calculated. This is done by using the effective detector separation, d, (see FIG. 2) and the coordinates of the crystals of the first and second sensor arrays 122, 123 which interacted with the coincident rays.

With reference to FIG. 4, the coordinates of the crystal in the first sensor array 122 is $X_U$, $Y_U$ and the coordinates of the crystal in the second sensor array 123 is $X_L$, $Y_L$. The event is thus localized on the line 130:

$$X_1 = X_L + a_1(X_U - X_L)$$

$$Y_1 = Y_L + a_i(Y_U - Y_L)$$

$$a_1 = Z_i/d \ldots (i=1 \text{ to } n) \tag{1}$$

It is not possible to determine the parameter $a_i$, which would locate the point of annihilation uniquely in 3-dimensional space. However, by assuming a value for $a_i$ and thus defining an imaging plane 132, the $X_i$ and $Y_1$ coordinates could be determined for that imaging plane 132. Supposing the detectors modules 120, 121 are 6 cm apart, 13 values for $a_1$ ranging from −3.0 cm to +3.0 cm are chosen. From equation 1, one can calculate 13 pairs ($X_1$, $Y_1$) of coordinates which correspond to the intersections of the line 130 given by equation 1 and the imaging planes 132 defined by Z=−3.0 to Z=3.0 in 5 mm intervals. These sets of coordinates can now be considered as points in a 128 by 128 by 16 matrix. All 16 of these matrix elements are augmented. [One does not know where the event really occurred, but by assigning the event (augmenting a memory location) at each level all possibilities are provided for]. Augmenting a memory location means or mechanism to add a small positive number to it. The magnitude of this number depends on the relative crystal pair efficiency, and the attenuation path length.

After placing the breast section to be examined between the two detectors modules 120, 121, the first or upper detector module 120 is lowered into place. The detector module separation, d, is measured with a position encoder 136. The position encoder 136 is read to calculate an angle scaling factor. Position determining look up tables are then calculated and saved in the data acquisition system's processor's tables which are part of the backprojecting means or mechanism 102. Acquisition takes place for a preset time, some 30–50 minutes after the IV FDG injection. When a coincidence is detected, the intersection points with possible 13 imaging planes are calculated by looking in the tables. The resulting 13 coordinates are presented to a modified gamma camera interface, which is set up to do a gated study. The 13 coordinate pairs are presented in turn, as if they were in separate phases of the cardiac cycle. Thus, all imaging planes 132 are augmented, via a read-modify-write memory cycle. Preferably, the point of intersection of the line and each imaging plane is proportional to the photon attenuation along that line divided by the product of the crystals' relative sensitivities.

At the end of the study, the data can be displayed on display means or mechanism 104 with conventional gamma camera display software. Note there is no reconstruction, as the memories contain the normalized projection data ready for display. Each imaging plane 132 contains an image of all data acquired throughout the study. The data has been, in effect "back-projected" onto all 13 imaging planes, by adding the same number to different locations in each imaging plane 132.

An analogy can be made with conventional X-ray tomography in which an X-ray tube and film move in an elliptical motion above and below the patient. The image is formed as an "in focus" image of the plane through which a line joining the focal spot and one point on the film passes through the same point in the patient. Attenuation from other points is blurred by the relative motion. In the present invention, each imaging plane 132 contains data from annihilations which truly occurred near that plane, and all others. As in the case of the X-ray tomography, the data which truly originated in that plane is in focus, that from other planes is blurred.

The 13 imaging planes 132 can now be examined one by one, or all can be displayed at once. The lower display threshold is raised until the background in normal tissue is almost "black". At this point, "hot spots" will appear in regions of high glucose metabolism, and "cold spots" in regions of low glucose metabolism. For either cold or hot spots, the section which contains the highest contrast, or best defined boundaries, is the one which localizes the abnormality best. Conventional Gamma Camera software for smoothing, contouring, measurement of area, and enhancement can be used to process and interpret the image.

Assuming that the same breast compression was used for a conventional mammogram, the conventional and emission mammographic images can be registered precisely.

To calibrate the apparatus 100, a plastic box having the dimensions of the largest compressed breast section likely to be imaged, is filled with FDG solution. The normal scanning technique is used and the table used to augment memory locations is filled with the value $Ke^{\mu p}$ (where $\mu$ is the linear attenuation coefficient for 511 keV gamma rays in water, 0.098 cm$^{-1}$ and p is the geometrical path length. The crystal efficiency tables in memory are all set to "1". Data is then acquired for about one hour.

At the end of the calibration scan all memory locations would have the same number of counts if all path lengths were equal, and all detector modules 120, 121 were equally efficient. They will have different numbers however due to counting statistics, and different crystal pair efficiencies. These will show up as variations in the calibration images. The line of response joining each crystal pair is then forward projected through all slices, and this is divided into the average value for all crystal pairs in order to derive the crystal efficiency table.

This calibration technique combines inter-crystal sensitivity and attenuation correction into the backprojection operation scaling, making possible real time image formation. The only difference is that rather than adding "1" to each memory location, a number which compensates for attenuation and inter-crystal sensitivity is added. Assuming the memory depth is only 16 bits, this number must be scaled to prevent quantization errors and over flows. It is anticipated that a number of the order of 100 would be used, with a range of 70 to 130. It may also be necessary to introduce a distortion correction as well in case the imaging response of the PMTs is nonlinear.

The apparatus 100 can be coupled to a minimally modified Gamma Camera acquisition and display computer capable of gated studies. All the calibration tables and line of response (LOR) calculations are self contained, but the highly developed Nuclear Medicine image processing software is well suited for use with the apparatus 100.

The fact that no image reconstruction is required, but spatial localization in all three axes is possible by back-projecting scaled values along each LOR, mimicking a gated study. This simple technique provides a simple imaging system with the best possible spatial resolution, and real time display of the images during formation. A similar approach to spatial localization has been discussed for applications unrelated to breast imaging (Performance Parameters of a Positron Imaging Camera, by G. Muehllehner, M. P. Buchin, and J. H. Dudek, IEEE Transactions on Nuclear Science, Vol. NS-23, No. 1, February 1976).

Figure 5:
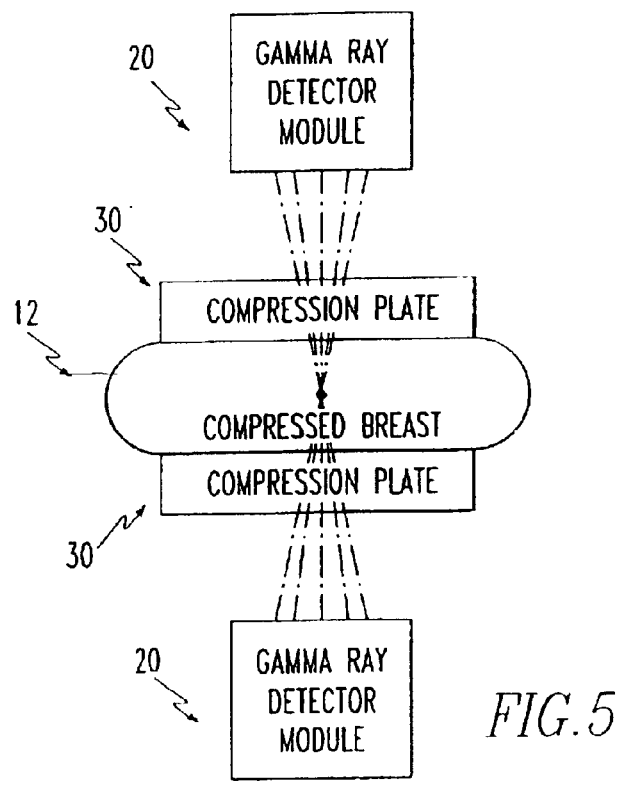
FIG. 5 is a schematic representation of a gamma-ray stereotactic imaging apparatus with two gamma-ray detector modules configured for coincidence detection or for dual-head single-emission acquisition.

The present invention also envisions use of dedicated instrumentation for emission mammography in conjunction with radiotracers that emit single gamma rays and/or photons. FIG. 5 shows a gamma-ray stereotactic imaging apparatus with two gamma-ray detector modules configured for coincidence detection or for dual-head single-emission acquisition. Radiotracers that decay by positron emission result in the production of a pair of gamma rays. Although such radiotracers are known to be highly accurate in the detection of breast cancer, recent reports in the literature have supported a role for single photon, gamma ray emitters such as Technetium-99m (A. Waxman et al., Journal of Nuclear Medicine, Vol. 34, Issue 5, Page 139P). Advantages to using such emitters include low cost and ease of availability as compared to positron emitters.

The apparatus 10 as described above would be adaptable for application to single photon emitters by using one or both of the detector modules 20 to detect activity from the compressed breast. (See FIGS. 5 and 6.)

Coincidence circuitry would not be required for single emission systems. Note that reports are present in the literature (Lee et al., Journal of Nuclear Medicine, Vol. 34, Issue 12, Pages 2095–2099, and A. Waxman et al., Journal of Nuclear Medicine, Vol. 34, Issue 5, Page 139P, incorporated by reference herein) describe the use of gamma cameras to detect activity from the breast from single photon and positron emitters. The difference between these reports and the present invention is that the present invention incorporates breast immobilization and/or compression during acquisition of data. Several advantages are realized as a result of this feature, which are enumerated as follows:

1. Since the breast contains few landmarks, internal details such as tumors will not be reproducibly localized unless immobilization/compression is used. Reproducible localization is essential if the emission image is to be used for interventions such as biopsy or placement of localizing needles for surgeons.

2. Immobilization/compression allows confident registration to be performed with x-ray images, thereby increasing diagnostic confidence in the ability of the emission image to characterize a lesion initially detected by x-rays.

3. Compression reduces the volume of tissue being imaged with the gamma-ray detectors to the region of clinical interest. This reduction in volume of tissue results in decreased attenuation of the gamma ray beam on its way from the lesion to the gamma-ray detector. Decreased attenuation will lead to increased count density, which is advantageous since the image is of higher diagnostic quality and since the dose to the patient can be reduced.

Figure 7:
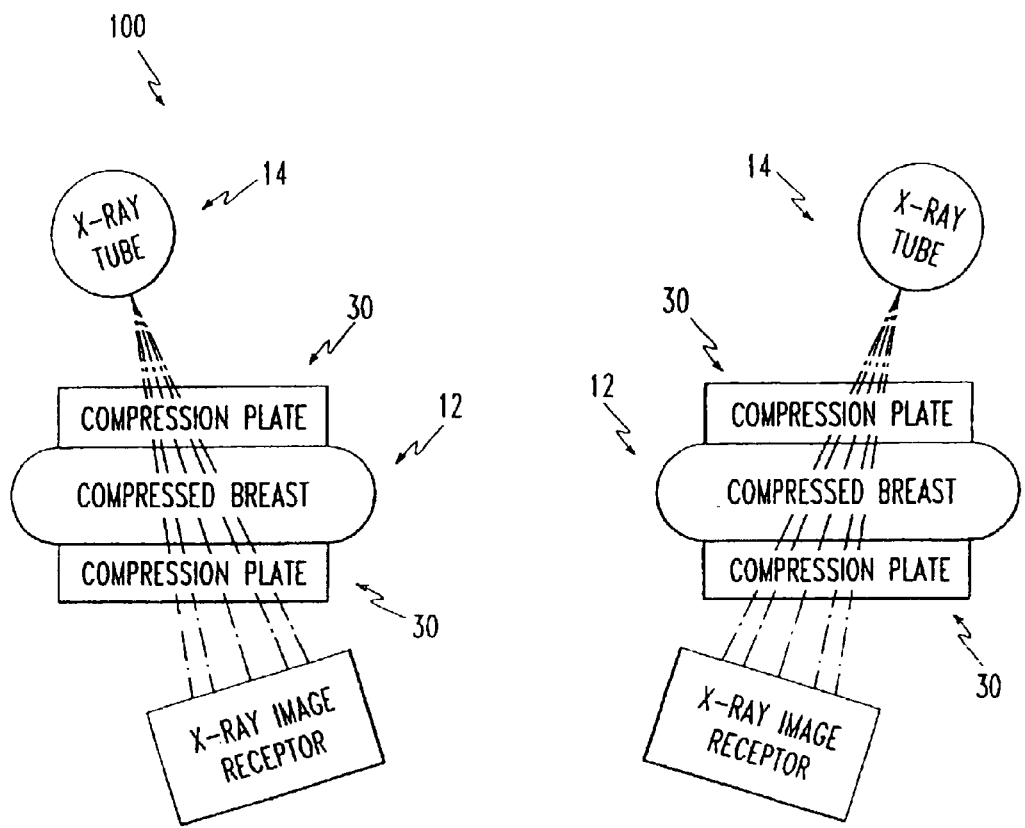
FIG. 7 is a schematic representation of an x-ray stereotactic imaging apparatus.

As shown in FIG. 7, stereotactic guidance is a technique employed by radiologists to direct biopsies using x-ray images. The technique consists of the acquisition of two projection images that differ in projection angle. The data afforded by having the two images allows the depth of a lesion to be assessed, just as the human brain can assess the depth of an object by integrating information from both eyes. As applied to mammography, the lack of internal stable structures in the breast require that the breast be immobilized during acquisition of both projections, without releasing compression between acquisitions. Several manufacturers (Fischer Corporation and Lorad Corporation) have designed mammography units in which software and display interfaces allow the stereotactic images to be inspected by a physician, and when a lesion is identified on both views a computer calculates the expected depth of the lesion. When the coordinates of the lesion are generated by the computer, the physician can enter the coordinates into a biopsy gun mount so that biopsies of the lesion can be reliably obtained.

As is known in the art, biopsy guns incorporate hollow needle assemblies that allow a core of tissue to be removed. Surgeons often request that hooks, needles, or dyes be placed in a suspicious lesion under mammographic guidance so that the surgeon can later identify the lesion in the operating room. Placement of such localizing hardware can be accomplished using stereotactic guidance.

Figure 8:
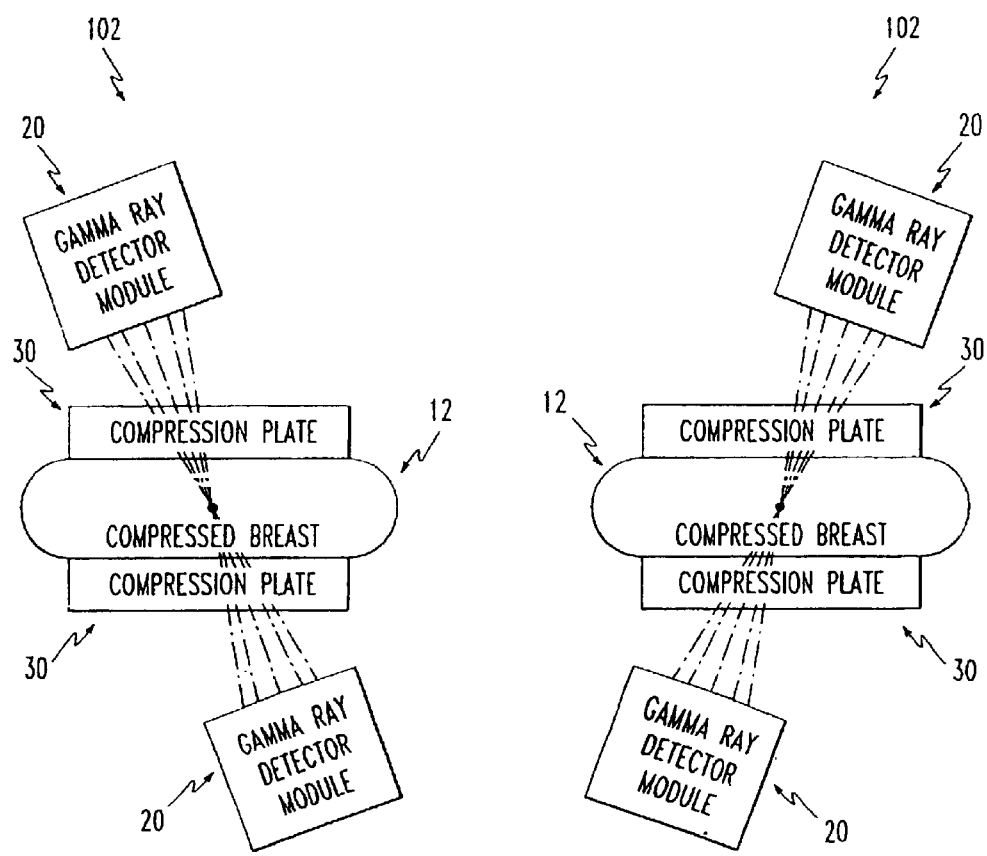
FIG. 8 is a schematic representation of a gamma-ray stereotactic imaging apparatus with mobile detector arrays.

One application of the present invention to use stereotactic guidance to provide projection images that can be used for stereotactic biopsy guidance. In a stereotactic x-ray mammographic unit (FIG. 7), the x-ray detector module travels a certain angle between the stereotactic views (usually 15 degrees) while the patient's breast 12 is under compression. In the present invention, as shown in FIG. 8, the gamma-ray detector modules 20 can be positioned so as to travel a specified angle as well.

Figure 9:
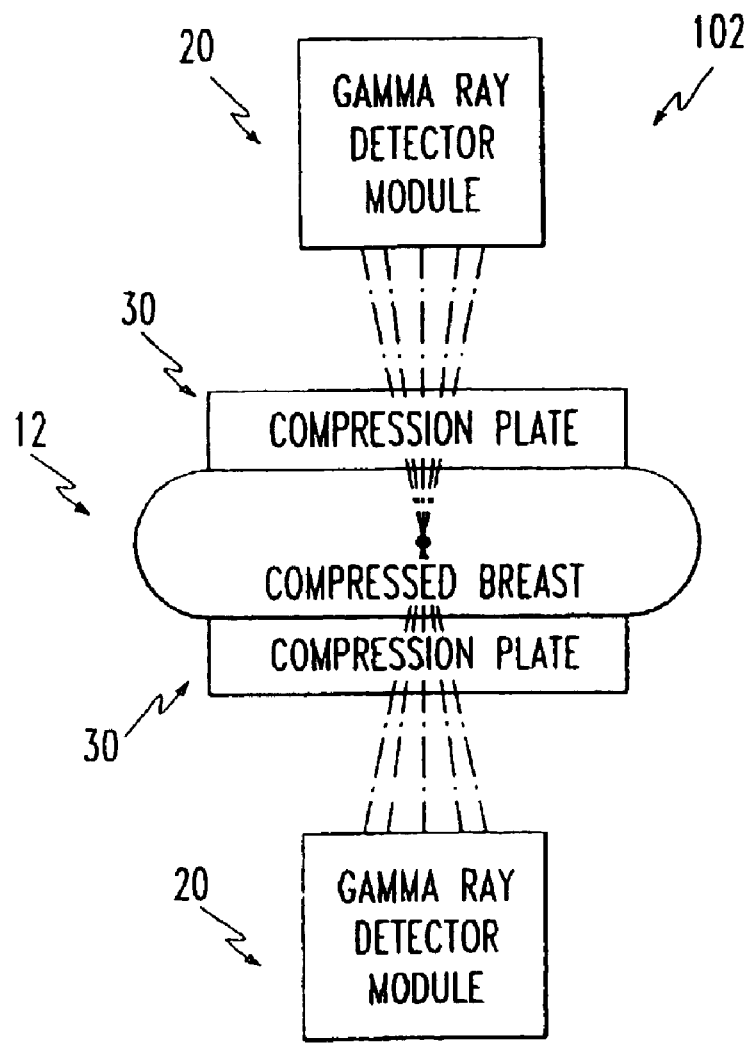
FIG. 9 is a schematic representation of a gamma-ray stereotactic imaging apparatus with stationary detector arrays.

Alternatively, since the gamma cameras obtain information from many projections, it is possible to have the gamma ray detector modules 20 remain in a single location while multiple projection views were obtained for stereotactic guidance (FIG. 9). The projections obtained from such projection views can be inspected by a human operator to detect a lesion. If the lesion is visible on more than one projection view, calculations similar to those performed for x-ray stereotactic guidance can be performed to determine the depth of the lesion. The coordinates of the lesion can then be used to guide biopsy.

Heretofore, stereotactic guidance has never been done using gamma cameras. The principal advantage of stereotactic guidance using gamma ray imaging relates to the requirement for sampling or excising lesions which might be only detectable using gamma-ray imaging techniques. It is a medical dictum that a detection method is not helpful if the results cannot be confirmed by biopsy, and current gamma cameras and positron emission tomography scanners are not well-suited to guide biopsies. This is due to the large size of these imaging devices and their relatively poor detection efficiencies which necessitate long acquisitions times. The requirement that a patient remain in compression for acquisition of the stereotactic views and for biopsy implies that high quality images be obtained in short times. The present invention allows this to happen because the detectors are so close to the breast, and because compression reduces the amount of attenuating tissue between the lesion and the detectors.

Note that the stereotactic capability of the invention allows biopsy guidance to be performed on the basis of the emission images alone or in conjunction with the x-ray images, since the gamma-ray detectors are in the same geometry as the conventional x-ray detectors. Thus an area of suspicion by x-ray criteria could be localized by x-ray stereotactic guidance and the presence or extent of the lesion confirmed by gamma-ray imaging prior to biopsy. Alternatively, if no lesions were identifiable by x-ray criteria, and the emission images identified a suspicious lesion, the biopsy could be guided on the basis of the emission images alone.

The present invention is an apparatus 10 for examining a body part 12. The apparatus comprises means or a mechanism 26 for immobilizing and compressing the body part and means or a mechanism 14 for providing an internal anatomical image of the body part. The apparatus also comprises means or a mechanism for detecting single gamma-rays emitted by a radiotracer infiltrated into the body party in an adjacent relationship with said means or mechanism for providing an internal anatomic image such that the body part 12 remains in the same position during and between anatomic and radiotracer imaging.

Figure 6:
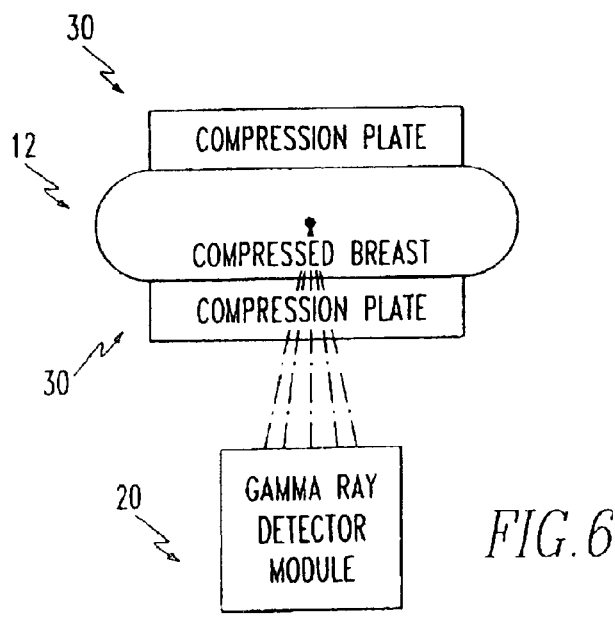
FIG. 6 is a schematic representation of a gamma-ray imaging apparatus with a gamma-ray detector module-configured for single-head single-emission acquisition.

In one embodiment, as shown in FIG. 6, the detecting means or mechanism includes a detector module 20 disposed on one side of the immobilizing means or mechanism 26. The detector module 20 preferably has at least one array of gamma ray sensitive material in communication with a position detector. In another embodiment, as shown in FIG. 5, the detecting means or mechanism includes a pair of detector modules 20 disposed one on each side of the immobilizing means or mechanism 26. Preferably, each detector module has at least one array of gamma-ray sensitive material in communication with a position detector. Preferably, the means or mechanism 14 for providing an anatomical image includes an x-ray source and x-ray recording medium.

The present invention is also an apparatus for examining a body part which comprises means or a mechanism 26 for immobilizing and compressing the body part and means or a mechanism for detecting single gamma-rays emitted by a radiotracer infiltrated into the body part 12. The detecting means or mechanism can include a detector module disposed on one side of the immobilizing means or mechanism or on both sides. If desired, there can be included means or a mechanism for providing an internal anatomical image of the body part, such as an x-ray device.

The present invention is also an apparatus for examining a body part 12 which comprises means or a mechanism 26 for immobilizing and compressing the body part 12 and means or a mechanism 100 for providing a stereotactic internal anatomical image of the body part (FIG. 7). The apparatus also comprises means or a mechanism 102 for providing a stereotactic physiological image of the body part in an adjacent relationship with the means or mechanism 100 for providing an internal anatomic image such that the body part remains in the same position during and between anatomic and radiotracer imaging.

Preferably, the means or mechanism 102 for obtaining a stereotactic physiological image includes a pair of detector modules 20 disposed one on each side of the immobilizing means or mechanism 26. In one embodiment, as shown in FIG. 8, the detector modules 20 are constructed to travel angularly about the body part 12 to provide projection images of the body part 12 from at least two different viewing angles, as is well known with x-ray stereotactic imaging. In another embodiment, the detector modules 20 are stationary with respect to the body part 12 and obtain multiple projection views of the body part 12.

The present invention is also an apparatus for examining a body part 12 which comprises means or a mechanism 26 for immobilizing and compressing the body part and means or a mechanism 102 for providing a stereotactic physiological image of the body part. As stated previously, detector modules 20 can be positioned to travel angularly about the body part 12 to provide projection images of the body part from at least two different viewing angles or detector modules can be stationary with respect to the body part 12 and multiple projection views of the body part are obtained to form a stereotactic image.

The present invention is also a method for examining a body part 12. The method comprises the steps of immobilizing the body part 12 in a preferred position such that the body part 12 is compressed and obtaining a stereotactic physiological image of the body part. Preferably, before the immobilizing step, there is the step of injecting the patient with a radiotracer which emits gamma rays and the step of obtaining a stereotactic physiological image includes the step of detecting gamma-rays with a pair of detector modules 20 disposed one on each side of immobilizing means or mechanism. Preferably, before the step of obtaining a stereotactic physiological image, there is the step of obtaining a stereotactic internal anatomical image of the body part 12. If desired, after the step of obtaining a stereotactic physiological image, there can be the step of directing a biopsy needle or gun into the body part 12 using the stereotactic physiological image for guidance and placement.

Moreover, after the step of obtaining an image, for example, a single image or stereotactic images, there can be the step of operating on the patient using the obtained radiotracer image or images for guidance and localization.

The present invention is also a method for examining a body part 12. The method comprises the steps of immobilizing the body part 12 in a preferred position such that the body part 12 is compressed and obtaining at least one physiological image of the body part. Preferably, before the immobilizing step, there is the step of injecting the patient with a radiotracer which emits gamma rays and the step of obtaining at least one physiological image includes the step of detecting gamma-rays with at least one detector module 20 on at least one side of the immobilizing means or mechanism. If desired, after the step of obtaining at least one physiological image, there can be the step of directing a biopsy needle or gun into the body part 12 using at least one physiological image for guidance and placement. After the step of obtaining the image or images, there can then be the step of operating on the patient using the image or images for guidance, localization, and preferably confirmation that the tumor has been removed completely. After the operating step, there can be the step of obtaining at least one image of surgical specimens to identify the presence of and the borders of tumors.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for examining a body part comprising the steps of:
   immobilizing and compressing the body part to provide reproducible localization of an area of interest in the body part and to improve diagnostic quality of an image of the body part; and
   obtaining at least one physiological image of the body part, wherein the body part is a prostate.

2. A method as described in claim 1 including after the step of obtaining the image, there is the step of operating on the patient using the image for guidance, localization, and confirmation that any tumor of the body part has been removed completely.

3. A method as described in claim 2, further including, after the operating step, the step of obtaining at least one image of surgical specimens to identify the presence of and the borders of tumors.

4. A method of examining a body part, comprising the steps of:
   injecting a patient with an agent whose concentration in the body part reflects the presence of malignant cells in the body part, said agent being a source of signal;
   immobilizing and compressing the body part to provide reproducible localization of a lesion in the body part and to improve diagnostic quality of an image of the body part;
   placing a detector capable of detecting signals emitted by the agent in proximity to the body part; and
   obtaining an image that displays the physiology of said body part based on signals emitted by the agent,
   wherein the body part is a prostate.

5. The method of claim 4, wherein said agent is a radiotracer that emits gamma rays.

6. The method of claim 5, wherein said radiotracer is 2-[F-18]-Fluoro-2 deoxy-D-glucose.

7. A method for examining a body part having tissue containing malignant cells, comprising the steps of:
   injecting a patient with an agent whose concentration in the body part depends on the physiological processes in the body part, said agent being a source of signal;
   immobilizing and compressing the body part to provide reproducible localization of an area of interest in the body part and to improve diagnostic quality of an image of the body part;
   obtaining an internal anatomical image of the body part;
   placing a detector capable of detecting signals emitted by the agent in proximity to said body part; and
   obtaining an image that displays the physiology of said body part based on signals emitted by the agent,
   wherein the body part is a prostate.

8. The method of claim 7, further comprising the step of using the images to locate and delineate the margins of regions containing the malignant cells in the body part.

9. The method of claim 8, further comprising the step of removing said tissue containing malignant cells.

10. The method of claim 9, further comprising the step of imaging the body part to confirm the absence of malignant cells in the body part after tissue removal.

11. A method of examining a body part, comprising the steps of:
    injecting a patient with an agent whose concentration in the body part depends on the physiologic processes of the body part, said agent being a source of signal;
    immobilizing and compressing the body part to provide reproducible localization of an area of interest in the body part and to improve diagnostic quality of an image of the body part;
    placing a detector capable of detecting signals emitted by the agent in proximity to the body part; and
    obtaining an image that displays the physiology of said body part based on signals emitted by the agent,
    wherein the body part is a prostate.

12. The method of claim 11, wherein said agent is a radiotracer that emits gamma rays.

13. The method of claim 12, wherein said radiotracer is 2-[F-18]-Fluoro-2 deoxy-D-glucose.

* * * * *